United States Patent
Fischer

[19]

[11] Patent Number: 5,816,804
[45] Date of Patent: Oct. 6, 1998

[54] FIBER-ENDED OPEN ORIFICE DELIVERY TIP

[75] Inventor: Dan E. Fischer, Sandy, Utah

[73] Assignee: Ultradent Products, Inc., South Jordan, Utah

[21] Appl. No.: 589,122

[22] Filed: Jan. 19, 1996

[51] Int. Cl.[6] .............................. A61C 5/04; A46B 11/02
[52] U.S. Cl. ............................... 433/90; 604/2; 604/311; 401/176; 401/286
[58] Field of Search .......................... 433/89, 90; 604/1, 604/2, 310, 311; 401/129, 171, 176, 177, 268, 271, 272, 282, 284, 286

[56] References Cited

U.S. PATENT DOCUMENTS

| | | |
|---|---|---|
| Re. 25,483 | 11/1963 | Lemos . |
| 767,469 | 8/1904 | Ziegler .................................... 401/176 |
| 2,145,570 | 1/1939 | Miettunen ............................... 401/176 |
| 2,293,211 | 8/1942 | Mureau .................................... 401/176 |
| 3,048,170 | 8/1962 | Lemos . |
| 3,359,992 | 12/1967 | Cishek et al. ........................... 401/171 |
| 3,417,762 | 12/1968 | Hall ......................................... 401/176 |
| 3,499,686 | 3/1970 | Landen et al. ........................... 401/268 |
| 4,199,270 | 4/1980 | Tomasini .................................. 401/286 |
| 4,672,953 | 6/1987 | DiVito . |
| 4,738,669 | 4/1988 | Vlock ....................................... 604/289 |
| 4,808,022 | 2/1989 | Iizuka et al. ............................. 401/171 |
| 4,963,046 | 10/1990 | Eguchi ..................................... 401/284 |
| 4,997,371 | 3/1991 | Fischer ...................................... 433/90 |
| 5,154,523 | 10/1992 | Devreeze ................................. 401/286 |
| 5,244,388 | 9/1993 | Frush ........................................ 433/90 |
| 5,246,371 | 9/1993 | Fischer ................................. 433/217.1 |
| 5,269,684 | 12/1993 | Fischer ...................................... 433/90 |
| 5,286,257 | 2/1994 | Fischer ...................................... 604/82 |

FOREIGN PATENT DOCUMENTS

| | | | |
|---|---|---|---|
| 3436472 | 4/1986 | European Pat. Off. | ............... 401/268 |
| 582361 | 2/1994 | European Pat. Off. | ............... 401/268 |
| 2288495 | 5/1976 | France | ................................... 401/284 |
| 2203636 | 10/1988 | United Kingdom | ................... 401/286 |
| WO 89/12428 | 12/1989 | WIPO . | |
| 9681 | 5/1994 | WIPO | ................................... 401/282 |

OTHER PUBLICATIONS

Advertisement for *Microbrush Disposable Applicators*, believed to be publicly available or known at least as early as Applicants' filing date.

*Primary Examiner*—Ralph A. Lewis
*Attorney, Agent, or Firm*—Workman Nydegger Seeley

[57] ABSTRACT

A delivery tip for use on a delivery device for applying a dental composition to tooth surfaces includes a tubular member having a proximal end and a distal end. The proximal end of the tubular member is coupled to the delivery device. A plurality of fibrous bristles are disposed on an outer periphery at the distal end of the tubular member. The fibrous bristles can be used in an agitating action to remove entrapped air bubbles from the applied composition such as an impression material. The fibrous bristles on the delivery tip can also be used to coat and spread the composition on tooth surfaces. With the fibrous bristles attached to the outer periphery at the distal end of the delivery tip, the composition can be delivered through the passageway in the tubular member without interference from the bristles.

48 Claims, 4 Drawing Sheets

FIBER-ENDED OPEN ORIFICE DELIVERY TIP

BACKGROUND OF THE INVENTION

1. The Field of the Invention

The present invention relates to an apparatus and method for delivering a dental composition to a tooth surface. More particularly, the present invention is directed to a hand operated delivery device having an open orifice, fiber-ended delivery tip capable of dispensing a dental composition directly onto a tooth surface.

2. The Relevant Technology

The development of modern instrumentation and materials, together with increased public awareness of the desirability of tooth preservation, have made cast restorations vital and frequently used elements in restorative and reconstructive prosthodontics dentistry. For years dentists have relied on indirect cast restorations such as crowns to maximize function, integrity, and aesthetics for compromised teeth. A primary step during cast restoration procedures is taking impressions of teeth for reconstruction.

There are many important dental compositions that need to be efficiently delivered to tooth surfaces during dental restorative procedures. Such dental compositions include hemostatic agents, etchants, bonding agents, disinfectants, sealants, and for indirect impression making, impression materials.

An apparatus for delivering a dental composition to tooth surfaces is disclosed in U.S. Pat. No. 4,997,371. The apparatus includes a syringe-type dispenser for holding a quantity of the dental composition and a removable applicator tip having bristles disposed within the passageway at the distal end of the tip. The bristles are held by the applicator tip primarily by the frictional grip that occurs at the distal end of the tip. Another apparatus for delivering dental compositions is disclosed in U.S. Pat. No. 5,269,684. This apparatus has a removable applicator tip with adjustable bristles disposed within the distal end of the tip. The bristles are slidably secured in a spiral passageway formed by a helical ridge inside the delivery tip.

The application of some dental compositions such as impression materials to tooth surfaces can be difficult through the brush tips because impression materials are highly viscous. It is nearly impossible to deliver impression materials with prior applicator tips since the resistance to flow is simply too great. Delivery of an impression material using these prior applicator tips is not effective since the bristles disposed within the passageway of the tips tend to choke off the tips, thus preventing flow of the impression material. Attempting to force the flow of the impression material or other highly viscous materials through a prior brush applicator tip may actually cause the fibers to be pushed out, expelling undesired quantities of the material into a patient's mouth.

In addition, the positioning of the bristles within the passageway of prior applicator tips causes the bristles to act as a filter, particularly with respect to any filler particles that are contained in the dental composition. Such filtering may change the physical properties of the dental composition as it is delivered to the tooth surface.

Another problem that can occur if one is applying an impression material to tooth surfaces with a conventional delivery device is that air bubbles remain entrapped within the impression material, particularly when a syringe is used in dispensing the impression material. Impression materials are formed from a base material that is mixed with a catalyst material. When the base material and catalyst material are mixed together, air bubbles are formed in the resulting impression material used to make a cast mold of teeth. These air bubbles can prevent complete reproduction of detail in the impression material, resulting in a poor cast mold of the teeth. The impression material is only useable for a few minutes once the base material and the catalyst material have been mixed, so it is important to remove entrapped air bubbles as soon as possible. In conventional delivery methods, after a quantity of impression material has been delivered around the prepared tooth, an air syringe is sometimes used to blow against the impression material. This helps to break up entrapped bubbles, but this is not always predictable and can result in additional air bubbles becoming entrapped in the impression material. In addition, time is wasted addressing this step while working time of the impression material is passing.

Accordingly, there is a need for an improved delivery tip that overcomes the above problems.

SUMMARY AND OBJECTS OF THE INVENTION

The present invention is directed to a delivery tip for applying a dental composition to a tooth surface. The delivery tip includes a tubular member having a proximal end and a distal end. A coupling means, such as a threaded portion or a Luer lock type connector, is located on the proximal end of the tubular member for releasably attaching the tubular member to a delivery device for the dental composition. A plurality of fibrous bristles are disposed on an outer periphery such as the outer surface and/or rim at the distal end of the tubular member. The fibrous bristles are attached to the outer periphery of the delivery tip so that a passageway extends through the delivery tip without interference from the fibrous bristles. In preferred embodiments, the fibrous bristles surround the outer surface and/or rim of the delivery tip adjacent to the distal end thereof, with at least a portion of the bristles extending a predetermined distance beyond the distal end.

The delivery tip of the present invention is particularly useful on a delivery device for dispensing dental compositions used in dental restorative procedures such as impression materials, bonding agents, sealants, and the like. The delivery tip is preferably made from a chemically inert material with respect to the dental compositions.

The construction of the delivery tip with the fibrous bristles on the outer periphery at the distal end thereof permits a free flow of the composition through the passageway of the delivery tip without interference from the bristles, thus preventing clogging of the tip. The fibrous bristles on the delivery tip permit an agitating action to remove air bubbles from the applied dental composition such as an impression material, reducing the amount of air entrapped within the impression material. The stimulation provided by the fibrous bristles also results in better adaptation of the impression material around tooth surfaces. The bristles may also act as with a brushing or scrubbing action which is advantageous for working other dental compositions into the tissues.

An apparatus for controlled delivery of a dental composition to a tooth surface includes a delivery device having the delivery tip of the present invention attached thereto. The delivery device includes a reservoir means for holding a quantity of the dental composition. The delivery tip is in fluid communication with the reservoir means. A means for controlled dispensing of the dental composition from the reservoir means to the distal end of the delivery tip in order to control the flow of the dental composition onto the tooth surface is also provided. The reservoir means is preferably a hollow syringe barrel, while the controlled dispensing means is preferably a plunger located within the syringe barrel. The delivery tip can be releasably or permanently attached to the reservoir means.

A method for delivery of a dental composition to a tooth surface using the delivery tip of the present invention includes the following steps. First, a quantity of the dental composition is loaded and held in a reservoir means such as a syringe barrel. The dental composition is then delivered through the delivery tip coupled to the reservoir means, with the delivery tip having a plurality of fibrous bristles disposed around the outer periphery at the distal end of the delivery tip. The dental composition is then agitated on the tooth surface with the fibrous bristles of the delivery tip to remove entrapped air bubbles. The fibrous bristles can also be used to coat and spread the dispensed composition on tooth surfaces.

The present invention has been developed in response to the present state of the art and, in particular, in response to problems and needs that have not been fully or completely solved by currently available dispensing devices. Accordingly, it is an overall object of the present invention to provide a novel delivery tip for use with a delivery device such as a dispensing syringe that can be used to both store and dispense various dental compositions.

A further object of the present invention is to provide a delivery tip that can be used with a delivery device to easily and efficiently dispense compositions that are highly viscous.

Another object of the present invention is to provide a delivery tip for applying a dental composition to a tooth surface that can be used to reduce entrapped air bubbles in the composition.

An additional object of the present invention is to provide a method of delivering a dental composition to a tooth surface using a novel delivery tip.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not to be considered limiting of its scope, the invention will be described and explained with additional specificity and detail through the use of the accompanying drawings in which.

DETAILED DESCRIPTION OF THE PREFERRED EMBODIMENTS

The present invention is directed to a delivery tip for applying a dental composition to a tooth surface. The delivery tip includes a tubular member with a plurality of fibrous bristles disposed on an outer periphery of the tip, such as the outer surface and/or distal rim at the distal end of the tubular member. An apparatus for controlled delivery of a dental composition to a tooth surface includes a delivery device having the delivery tip of the present invention attached thereto.

Figure 1:
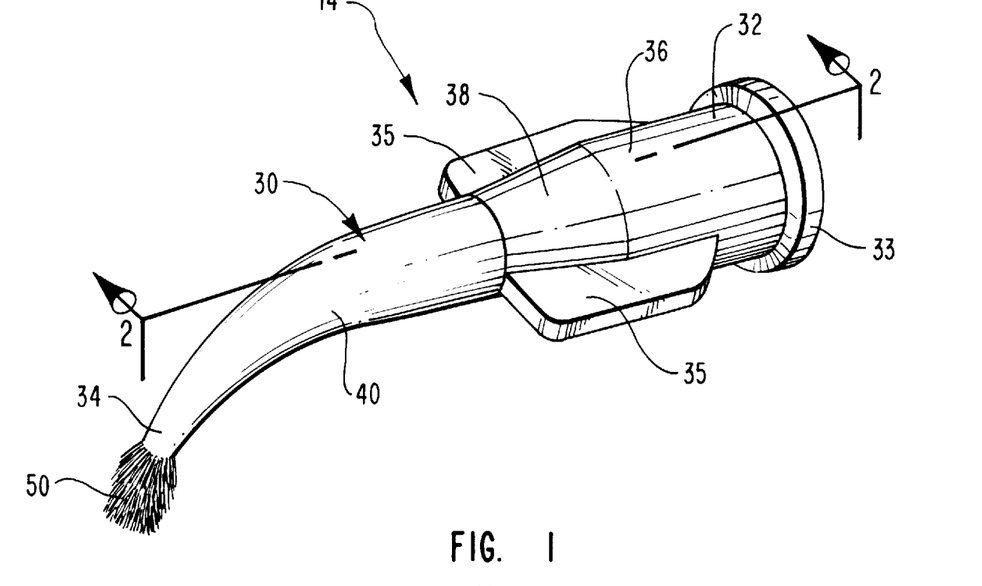
FIG. 1 is a perspective view of one embodiment of the delivery tip of the present invention.
Figure 2A:
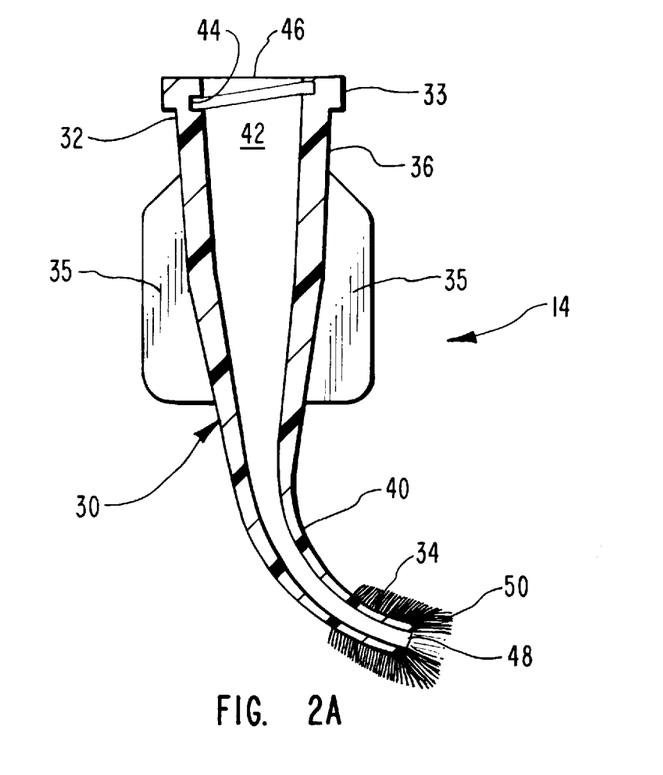
FIG. 2A is a longitudinal cross-sectional view of the embodiment of FIG. 1 taken along lines 2—2.
Figure 2B:
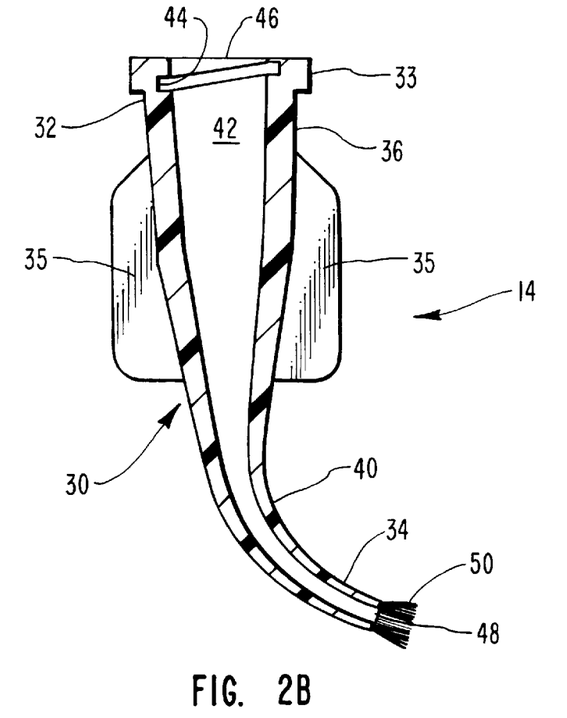
FIG. 2B is a longitudinal cross-sectional view of an alternative embodiment of the delivery tip of FIG. 1.
Figure 3:
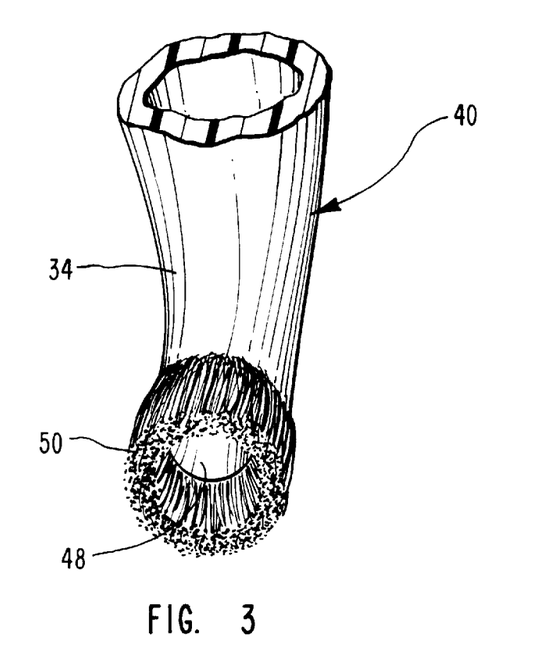
FIG. 3 is an enlarged end view of the delivery tip of FIG. 1.
Figure 4:
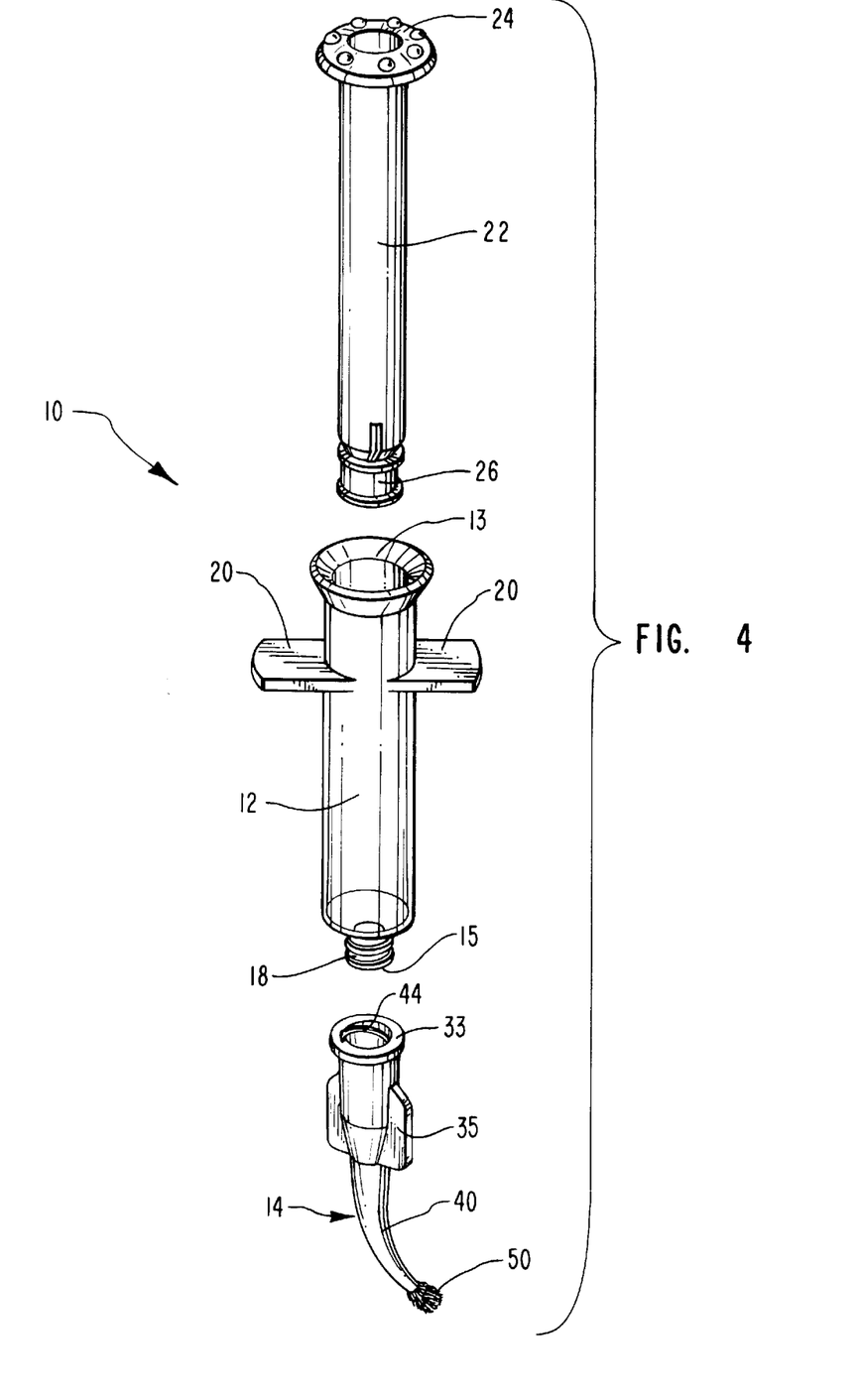
FIG. 4 is an exploded perspective view of the delivery tip of FIG. 1 and a syringe apparatus that can be used therewith.
Figure 5:
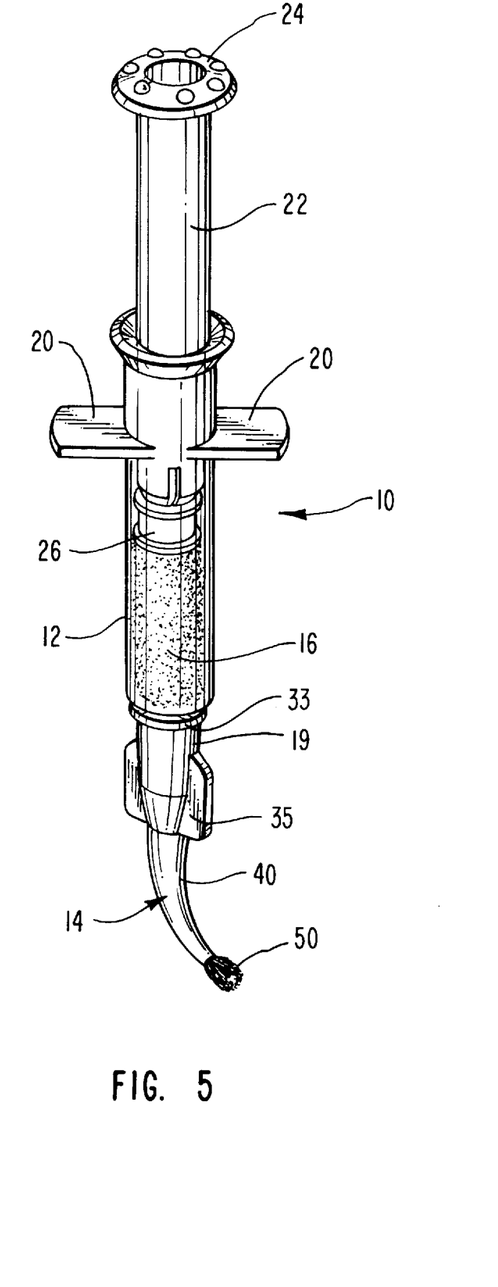
FIG. 5 is a perspective view of the delivery tip and syringe apparatus of FIG. 4 in an assembled condition.
Figure 6:
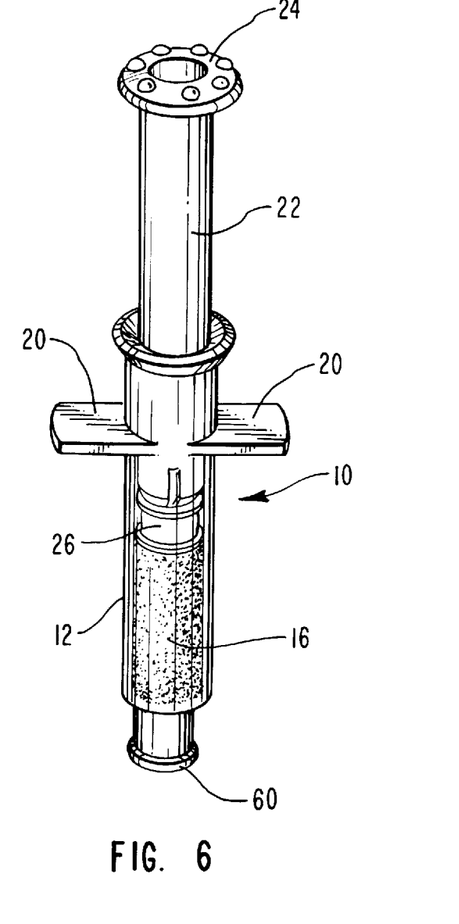
FIG. 6 is a perspective view of the syringe apparatus of FIG. 5 with the delivery tip replaced by a cap.

Referring to the drawings, where like parts are designated with like numerals throughout, FIGS. 1–3 illustrate a delivery tip 14 according to the present invention. FIGS. 4–6 illustrate a delivery device in the form of a syringe 10 that can be used with delivery tip 14.

Turning first to FIG. 4, an exploded view of syringe 10 and delivery tip 14 in unassembled condition is illustrated. The syringe 10 includes a reservoir means for holding a quantity of the dental composition. A preferred embodiment of the reservoir means is a hollow syringe barrel 12. The syringe barrel 12 has a loading end 13 and a discharge end 15. The syringe barrel 12 is generally cylindrical in shape and is adapted for holding a quantity of a dental composition 16, as shown in FIGS. 5 and 6. The dental composition 16 can be dental impression materials, hydrophilic bonding agents, sealing agents, antimicrobial agents, etching agents, hydrophobic resins, flowable composites, pot and fissure sealants, and the like.

A pair of finger flanges 20 protrude from the outer surface of syringe barrel 12, which aid in gripping barrel 12 while dispensing composition 16. The outer surface of syringe barrel 12 can also be provided with gradient markings to aid in dispensing a precise amount of composition 16.

The syringe 10 also includes a means for controlled dispensing of the dental composition from the reservoir means to the distal end of delivery tip 14 in order to control the flow of the dental composition onto tooth surfaces. In a preferred embodiment, the controlled dispensing means is a plunger 22 that is longitudinally slidable within syringe barrel 12. The plunger 22 has a circular flange 24 at the outer end thereof. A plunger head 26 is disposed at the opposite end of plunger 22 from circular flange 24. The plunger head 26 is constructed of a resilient material such that the outer edge of plunger head 26 is contiguous with the inner wall of syringe barrel 12. In addition, plunger head 26 is preferably constructed of a material that is nonreactive with the dental composition. Markings may be placed on plunger 22 to identify the volume of dental composition used or remaining.

It will be appreciated that other means may be used to control dispensing of a dental composition onto a tooth surface. For example, the delivery tip of the invention may be adapted for capsule use or for squeeze bulb use.

The discharge end 15 of syringe barrel 12 includes a coupling means for attaching delivery tip 14 to syringe 10. The coupling means includes in one embodiment a syringe threaded portion 18 that is complimentary with a corresponding tip threaded portion 44 on delivery tip 14 as discussed in greater detail below. Other means may be used to attach delivery tip 14 to syringe barrel 12, which will also be discussed in further detail below.

FIGS. 1, 2A and 2B illustrate delivery tip 14 in greater detail. The delivery tip 14 includes a tubular member 30 having a proximal end 32 and a distal end 34. The tubular member 30 includes a cylindrical hub 36 toward proximal end 32, and a tapered nozzle 40 toward distal end 34. A conical section 38 is disposed between and integrally formed with hub 36 and nozzle 40. The outer diameter of delivery tip 14 thus gradually decreases in size from proximal end 32 to distal end 34. The nozzle 40 may be curved as shown, or straight.

A pair of fins 35 protrude from the outer surface of tubular member 30. The fins 35 provide convenience in attaching delivery tip 14 onto syringe barrel 12. A circular lip 33 surrounds the outer periphery of delivery tip 14 at proximal end 32. The lip 33 provides a fluid sealing surface to prevent leakage of composition 16 when delivery tip 14 is coupled to syringe barrel 12

A coupling means for detachably coupling delivery tip 14 to syringe barrel 12 is provided at proximal end 32 of tubular member 30. One presently preferred embodiment of the coupling means includes tip threaded portion 44 formed of female threads on the interior surface of delivery tip 14 at proximal end 32. The tip threaded portion 44 is shown in FIGS. 2A, 2B and 4. The tip threaded portion 44 can be coupled with complementary syringe threaded portion 18 formed with male threads on discharge end 15 of syringe barrel 12.

It will be appreciated that the coupling means can be implemented using various other equivalent structures and be within the intended scope of the invention. For example, delivery tip 14 could be formed with male threads and discharge end 15 of syringe barrel 12 could be formed of complementary female threads. In addition, delivery tip 14 could be detachably coupled to syringe barrel 12 by way of a Luer-lock type attachment in which delivery tip 14 utilizes a female Luer connector and discharge end 15 of syringe barrel 12 uses a male Luer connector or vice versa. Another arrangement that could be used is a press fit attachment of delivery tip 14 to syringe barrel 12. Any arrangement can be used wherein delivery tip 14 detachably couples to discharge end 15 of syringe barrel 12.

While in the embodiments illustrated delivery tip 14 is removable, it is possible in an alternative embodiment within the scope of the present invention to permanently secure delivery tip 14 to syringe barrel 12. Thus, delivery tip 14 may be integrally molded as part of syringe barrel 12 or may irreversibly snap onto syringe barrel 12. In such an embodiment, syringe barrel 12 could be configured to hold only a sufficient quantity of a dental composition for a single application. Thereafter, the device could be discarded.

As illustrated in FIGS. 2A and 2B, the interior of delivery tip 14 forms a tapered passageway 42. The passageway 42 narrows from an inlet orifice 46 at proximal end 32 toward an outlet orifice 48 at distal end 34. The passageway 42 can be formed with any desired cross-sectional shape, such as circular, elliptical, square, rectangular, or polygonal.

As depicted in FIGS. 2A and 3, a plurality of fibrous bristles 50 are disposed around the outer periphery including on the outer surface and distal rim of nozzle 40 at distal end 34 of delivery tip 14. The fibrous bristles 50 are disposed on and surround the outer surface and distal rim of nozzle 40 so as not to obstruct outlet orifice 48 of delivery tip 14. While the illustrated embodiment of FIG. 3 depicts fibrous bristles 50 as completely surrounding the outer periphery of nozzle 40 at distal end 34, it is possible that fiber bristles could be disposed on delivery tip 14 in other ways. For example, fiber bristles could be disposed in spaced apart clumps around the outer periphery of nozzle 40 at distal end 34. In addition, as shown in FIG. 2B in an alternative embodiment, fibrous bristles 50 can be disposed on and around only the distal rim of distal end 34.

At least a portion of fibrous bristles 50 extend a predetermined distance beyond the distal rim surrounding outlet orifice 48 of delivery tip 14 at distal end 34. Such a distance can be in the range from about 0.3 mm to about 3 mm, depending on the length of the fibers used for the bristles.

The delivery tip of the invention can be made with longer bristles or with shorter bristles. For example, the delivery tip 14 made with longer bristles is useful in applying compositions such as sealing agents that need to be painted onto tooth surfaces. The delivery tip 14 made with shorter bristles is useful in delivering and agitating impression and other appropriate materials. The fiber bristle length for fibrous bristles 50 is in the range from about 0.3 mm to about 3 mm, preferably from about 0.5 mm to about 2 mm. In a preferred embodiment, the fiber bristle diameter is in the range from about 0.02 mm to about 0.2 mm, and more preferably in the range from about 0.06 mm to about 0.09 mm.

The fibrous bristles 50 are preferably constructed of reasonably soft fibers so as not to irritate target dental surfaces. Both natural and synthetic fibers may be used to form fibrous bristles 50. Suitable natural fibers include cotton fibers, while suitable synthetic fibers include nylon and polyester fibers. In addition, various injection moldable plastics can be employed to form the bristles using standard injection molding techniques.

The fibrous bristles 50 can be attached to the outer surface and/or rim of delivery tip 14 at distal end 34 by various methods. One method is by adhesive attachment of fibers to the outer periphery at the distal end of the delivery tip. An adhesive material is applied to the outer surface and/or rim of the delivery tip where fiber attachment is desired. An appropriate quantity of fibers is then contacted with the adhesive material on the delivery tip. The adhesive is allowed to harden, thereby securing the fibers to the outer periphery at the distal end of the delivery tip.

Another method of fiber attachment is to sonically weld or bond the fibers to the outer periphery at the distal end of the delivery tip using standard ultrasonic welding or bonding techniques. A further method of fiber attachment is to use a thermoforming plastic material to make the delivery tip and to cause the fibers to electrostatically attach to the outer periphery at the distal end of the delivery tip. An additional method of fiber attachment is to injection mold the fibers onto the desired outer periphery at the distal end of the delivery tip. In this method, the fibers and delivery tip are injection molded together from a plastic material so that the fibrous bristles are integrally formed on the outer surface and/or rim at the distal end of the delivery tip.

FIG. 5 illustrates delivery tip 14 attached to syringe 10. When using delivery tip 14 with a delivery device such as syringe 10, plunger 22 is inserted into loading end 13 after dental composition 16 has been preloaded in syringe barrel 12. The plunger 22 is then advanced inwardly so that plunger head 26 presses against composition 16, thereby causing composition 16 to flow out of discharge end 15 of syringe barrel 12 and into passageway 42 of delivery tip 14. The composition 16 flows through passageway 42 of delivery tip 14 without obstruction since fibrous bristles 50 are disposed on the outer surface of nozzle 40. Thus, delivery tip 14 does not become clogged during delivery of composition 16 to a tooth surface.

As illustrated in FIG. 6, delivery tip 14 may be removed from syringe 10 and replaced with a cap 60. The syringe barrel 12 may be marketed prefilled with composition 16 and sealed with cap 60. Alternatively, syringe barrel 12 may be filled with composition 16 by removing cap 60 and drawing the desired amount of composition 16 into syringe barrel 12 from an appropriate storage container. In addition, composition 16 can be loaded into syringe barrel 12 through loading end 13. During use of syringe 10, cap 60 is removed from syringe barrel 12 and replaced with delivery tip 14. After composition 16 is applied to a tooth surface, delivery tip 14 is removed from syringe barrel 12 and discarded. it The cap 60 is then replaced on syringe barrel 12, and syringe 10 is stored until the dental composition is needed in the future. If used properly, syringe barrel 12 should still be clean. Nevertheless, syringe barrel 12 may be disinfected if necessary.

Substantially enhanced delivery of a dental composition is accomplished by the delivery tip of the present invention. For example, delivery of a viscous composition, which may or may not be viscous due to a filler, is virtually impossible to express through prior delivery tips which have bristles disposed within the passageway of the tips. Such a viscous composition is easily expressed through the open passageway of the delivery tip of the present invention and any filler particles in the composition are not filtered out.

The delivery tip of the invention can be constructed of a rigid plastic material, as well as other suitable materials such as metal or glass. The delivery tip can also be made with a combination of materials. For example, hub 36 can be made from a plastic material and nozzle 40 can be made from a metallic material.

It is important that the components of the delivery tip and the delivery device such as a syringe be constructed of materials that will not react with a dental composition used therewith. In addition, the dental composition should not adhere to the construction materials used. Since many dental compositions are light sensitive, the construction materials used may be light-resistive. For example, various colored plastics that tend to filter out light can be employed in making the delivery tip and syringe.

In addition, different colored plastics may be used to identify the type of dental composition within the syringe. Alternatively, printing or other identifying markings on the syringe may be used to identify the type of dental composition therein.

Although the above discussion has described an apparatus used for applying dental compositions to tooth surfaces, it will be appreciated that the apparatus of the present invention may be adapted for applying other materials to various surface types.

A method for delivery of a dental composition to tooth surfaces includes loading and holding a quantity of the dental composition in a reservoir means such as a syringe barrel. The dental composition is then delivered from the reservoir means through a delivery tip coupled to the reservoir means, with the delivery tip having a plurality of fibrous bristles disposed around an outer periphery at the distal end of the delivery tip. The dispensed dental composition on tooth surfaces can be agitated with the fibrous bristles on the delivery tip to remove entrapped air bubbles or to scrub the tooth structure, or work the composition into the tissues. The fibrous bristles can also be used to coat and spread the dispensed dental composition on tooth surfaces.

The delivery tip of the invention is particularly useful for dispensing impression materials onto tooth surfaces. A problem that occurs when applying impression materials to tooth surfaces with conventional delivery devices is that air bubbles remain entrapped within the impression material. By agitating the dispensed impression material with the fibers on the outer periphery of the delivery tip of the invention, entrapped air bubbles are removed from the impression material.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A delivery tip for use in combination with a delivery device such as a syringe, comprising a reservoir means for holding a quantity of a dental composition for restorative or reconstructive dental procedures and a means for controlled dispensing of the dental composition from the reservoir means and through the delivery tip in order to apply in a precise, controlled fashion the dental composition to a small area such as a relatively small region of a tooth surface that is to be restored or reconstructed, the delivery tip comprising:

(a) a tubular member having a proximal end and a tubular distal end, the tubular member having a passageway extending from an inlet orifice at the proximal end to an outlet orifice with a distal rim at the tubular distal end, the tubular distal end being of a size and being configured for precise, controlled delivery of the fluid, the tubular distal end having an outer periphery surface located near said outlet orifice;

(b) coupling means on the proximal end for adapting said tubular member for releasable attachment to a delivery device; and (c) a plurality of fibrous bristles disposed on and surrounding the outer surface and distal rim of the outlet orifice such that said bristles permit a free flow of the fluid out of said outlet orifice without any substantial interference from said bristles.

2. The delivery tip of claim 1, wherein said tubular member tapers in width from the proximal end to the distal end.

3. The delivery tip of claim 1, wherein said tubular distal end is curved.

4. The delivery tip of claim 1, wherein said coupling means is a press fit connector adapted for frictional coupling to the delivery device.

5. The delivery tip of claim 1, wherein said coupling means comprises a threaded portion formed on the proximal end of the tubular member that is complementary with a threaded portion formed on the delivery device.

6. The delivery tip of claim 1, wherein said outer periphery surface near said outlet orifice comprises an outer surface located around said tubular distal end such that said fibrous bristles are disposed on said outer surface and extend from said outer surface.

7. The delivery tip of claim 1, wherein said outer periphery surface near said outlet orifice comprises a distal rim surface located around said outlet orifice such that said fibrous bristles extend from said distal rim surface beyond the tubular distal end.

8. The delivery tip of claim 1, wherein at least a portion of said fibrous brisles extends from the tublar distal end of said tubular member a distance in a range from about 0.3 mm to about 3 mm.

9. The delivery tip of claim 1, wherein each of said fibrous bristles has a diameter in a range from about 0.02 mm to about 0.2 mm.

10. The delivery tip of claim 1, wherein said fibrous bristles are constructed from natural fibers.

11. The delivery tip of claim 1, wherein said fibrous bristles are constructed from a synthetic material.

12. The delivery tip of claim 1, wherein the tip is constructed of a plastic material.

13. An apparatus for precise, controlled delivery of a fluid to a small area such as a relatively small region of a tooth surface, comprising:
(a) reservoir means for holding a quantity of the fluid;
(b) a delivery tip having a proximal end and a tubular distal end, the delivery tip having a passageway extending from an inlet orifice at the proximal end to an outlet orifice with a distal rim at the tubular distal end, the tubular distal end being of a size and being configured for precise, controlled delivery of the fluid, the tubular distal end having an outer periphery surface located near the outlet orifice, the passageway being in communication with said reservoir means such that the fluid can flow through from the reservoir means into the inlet orifice and through the passageway;
(c) a plurality of fibrous bristles disposed on and surrounding the outer surface and distal rim of the outlet orifice such that said bristles permit a free flow of the fluid out of said outlet orifice without any substantial interference from said bristles; and
(d) means for controlled dispensing of the fluid from said reservoir means to cause the flow of the fluid from the reservoir means, into the inlet orifice, through the passageway and then out of the outlet orifice.

14. The apparatus of claim 13, wherein said reservoir means comprises a hollow syringe barrel.

15. The apparatus of claim 14, wherein said controlled dispensing means comprises a plunger located within said syringe barrel.

16. The apparatus of claim 13, wherein said delivery tip tapers in width from the proximal end of the delivery tip to the distal end.

17. The apparatus of claim 13, wherein said delivery tip is releasably coupled to said reservoir means.

18. The apparatus of claim 13, wherein said delivery tip is threadably coupled to said reservoir means.

19. The apparatus of claim 13, wherein said delivery tip is frictionally coupled to said reservoir means with a press fit connector.

20. The apparatus of claim 13, wherein said delivery tip is permanently secured to said reservoir means.

21. The apparatus of claim 13, wherein said outer periphery surface near said outlet orifice comprises a distal rim surface located around said outlet orifice such that said fibrous bristles extend from said distal rim surface and extend beyond the tubular distal end.

22. The apparatus of claim 13, wherein at least a portion of said fibrous bristles extends from the tubular distal end of said delivery tip a distance in a range from about 0.3 mm to about 3 mm.

23. The apparatus of claim 13, wherein each of said fibrous bristles has a diameter in a range from about 0.02 mm to about 0.2 mm.

24. The apparatus of claim 13, wherein said fibrous bristles are constructed from natural fibers.

25. The apparatus of claim 13, wherein said fibrous bristles are constructed from a synthetic material.

26. The apparatus of claim 13, wherein said delivery tip is constructed of a plastic material.

27. The apparatus of claim 13, wherein said outer periphery surface near said outlet orifice comprises an outer surface located around said tubular distal end such that said fibrous bristles extend from said outer surface.

28. An apparatus for precise, controlled delivery of a fluid to a small area such as a relatively small region of a tooth surface, comprising:
(a) a syringe barrel for holding a quantity of the fluid, said syringe barrel having a discharge end;
(b) a plunger slidably disposed within said syringe barrel for controlled dispensing of the fluid from the discharge end of said syringe barrel;
(c) a delivery tip having a proximal end and a tubular distal end, the delivery tip having a passageway extending from an inlet orifice at the proximal end to an outlet orifice with a distal rim at the tubular distal end, the tubular distal end being of a size and being configured for precise, controlled delivery of the fluid, the tubular distal end having all outer periphery surface located near the outlet orifice, said delivery tip being coupled to the discharge end of said syringe barrel at the proximal end of said delivery tip, the passageway being in communication with said syringe barrel such that the fluid can flow through from the syringe barrel into the inlet orifice and through the passageway; and
(d) a plurality of fibrous bristles disposed on and surrounding the outer surface and distal rim of the outlet orifice such that said bristles permit a free flow of the fluid out of said outlet orifice without any substantial interference from said bristles.

29. The apparatus of claim 28, wherein said delivery tip tapers in width from the proximal end of the delivery tip to the distal end.

30. The apparatus of claim 28, wherein said proximal end of said delivery tip is releasably coupled to the discharge end of said syringe barrel.

31. The apparatus of claim 28, wherein said proximal end of said delivery tip is threadably coupled to the discharge end of said syringe barrel.

32. The apparatus of claim 28, wherein said proximal end of said delivery tip is frictionally coupled to the discharge end of said syringe barrel with a press fit connector.

33. The apparatus of claim 28, wherein said proximal end of said delivery tip is permanently secured to the discharge end of said syringe barrel.

34. The apparatus of claim 28, wherein said outer periphery surface near said outlet orifice comprises a distal rim surface located around said outlet orifice such that said fibrous bristles extend from said distal rim surface and beyond the tubular distal end.

35. The apparatus of claim 28, wherein at least a portion of said fibrous bristles extends from the tubular distal end of said delivery tip a distance in a range from about 0.3 mm to about 3 mm.

36. The apparatus of claim 28, wherein each of said fibrous bristles has a diameter in a range from about 0.02 mm to about 0.2 mm.

37. The apparatus of claim 28, wherein said fibrous bristles are constructed from natural fibers.

38. The apparatus of claim 28, wherein said fibrous bristles are constructed from a synthetic material.

39. The apparatus of claim 28, wherein said outer periphery near said outlet orifice comprises an outer surface located around said tubular distal end such that said fibrous bristles extend from said outer surface.

40. A method for delivery of a dental composition onto a relatively small region of a tooth surface in a precise, controlled fashion, comprising the steps of:
  (a) holding a quantity of the dental composition in a reservoir means for holding the dental composition, the reservoir means being coupled to a proximal end of a delivery tip;
  (b) delivering the dental composition from the reservoir means onto a relatively small region of a tooth surface in a precise, controlled fashion by dispensing the dental composition from the reservoir means through a passageway in the delivery tip that extends from an inlet orifice with a distal rim located in the proximal end of said delivery tip to an outlet orifice in a tubular distal end of said delivery tip, the delivery tip including a plurality of fibrous bristles disposed on and surrounding the outer surface and distal rim of the outlet orifice in a configuration that permits the dental composition to freely flow out of said outlet orifice without any substantial interference from said bristles; and
  (c) agitating the dental composition on the tooth surface with the fibrous bristles.

41. The method of claim 40, wherein the reservoir means comprises a syringe barrel and wherein the dental composition is dispensed from the syringe barrel by a plunger slidably disposed within the syringe barrel.

42. The method of claim 41, wherein the step of delivering the dental composition from the syringe barrel is achieved by depressing the plunger so as to force the dental composition through the inlet orifice, into the passageway of the delivery tip and out of the outlet orifice.

43. The method of claim 40, wherein said outer periphery surface near said outlet orifice comprises an outer surface located around said tubular distal end such that the fibrous bristles extend from the outer surface.

44. The method of claim 40, wherein the fibrous bristles are constructed from natural fibers.

45. The method of claim 40, wherein said fibrous bristles are constructed from a synthetic material.

46. The method of claim 40, wherein the delivery tip is constructed of a plastic material.

47. The method of claim 40, wherein said outer periphery surface near said outlet orifice comprises a distal rim surface located around said outlet orifice such that said fibrous bristles are disposed on the distal rim and extend beyond the tubular distal end.

48. A method for delivery of a dental composition onto a relatively small region of a tooth surface in a precise, controlled fashion, comprising the steps of:
  (a) holding a quantity of the dental composition in a reservoir means for holding the dental composition, the reservoir means being coupled to a proximal end of a delivery tip;
  (b) delivering the dental composition from the reservoir means onto a relatively small region of a tooth surface in a precise, controlled fashion by dispensing the dental composition from the reservoir means through a passageway in the delivery tip that extends from an inlet orifice located in the proximal end of said delivery tip to an outlet orifice with a distal rim in a tubular distal end of said delivery tip, the delivery tip including a plurality of fibrous bristles disposed on and surrounding the outer surface and distal rim of the outlet orifice in a configuration that permits the dental composition to freely flow out of said outlet orifice without any substantial interference from said bristles; and
  (c) coating the dental composition on the tooth surface with the fibrous bristles.

* * * * *